United States Patent [19]

Kuhn et al.

[11] Patent Number: 5,138,087
[45] Date of Patent: Aug. 11, 1992

[54] 1,1,1-TRIFLUORO-2-PROPENE COMPOUNDS AND A METHOD FOR THEIR PREPARATION

[75] Inventors: David G. Kuhn, Newton, Pa.; Kenneth A. Martin, Lawrenceville, N.J.

[73] Assignee: American Cyanamid Company, Stamford, Conn.

[21] Appl. No.: 736,169

[22] Filed: Jul. 26, 1991

Related U.S. Application Data

[62] Division of Ser. No. 560,403, Jul. 31, 1990, Pat. No. 5,068,390.

[51] Int. Cl.$^5$ .................. C07C 255/00; C07C 69/63; C07C 53/21; C07C 49/04
[52] U.S. Cl. .................................. 558/461; 558/462; 560/227; 562/605; 568/418
[58] Field of Search ................ 558/461, 462; 560/227; 562/605; 568/418

[56] References Cited

U.S. PATENT DOCUMENTS 3,681,414  8/1972  Sakuragi et al. ............... 558/461
4,289,711  9/1981  Lee .................................. 560/227
4,992,577  2/1991  Lantzsch et al. ................ 558/414

OTHER PUBLICATIONS

CA 101: 110327y Preparation of . . . organometallic compounds. Ishikawa et al. 1984, p. 603.
CA 112:177602e Preparation of . . . of esters. Thenappan et al. 1989, p. 644.

Primary Examiner—Mary C. Lee
Assistant Examiner—Joseph K. McKane
Attorney, Agent, or Firm—John W. Hogan, Jr.

[57] ABSTRACT 1,1,1-trifluoro-2-propene compounds which are useful in preparation of insecticidal, acaricidal and nematicidal arylpyrrole compounds are described. A method for the preparation of 1,1,1-trifluoro-2-propene compounds is presented.

5 Claims, No Drawings

1,1,1-TRIFLUORO-2-PROPENE COMPOUNDS AND A METHOD FOR THEIR PREPARATION

This is a divisional of co-pending application Ser. No. 07/560,403, filed on Jul. 31, 1990, now U.S. Pat. No. 5,068,390.

BACKGROUND OF THE INVENTION

The present invention describes 1,1,1-trifluoro-2-propene compounds which are useful in the preparation of insecticidal, acaricidal and nematicidal arylpyrrole compounds. The arylpyrrole compounds are described in copending patent application Ser. No. 392,495, filed on Aug. 11, 1989.

N. Ishikawa et al, Journal of Flourine Chemistry, 24, pp 419–430 (1984) disclose the preparation of certain trifluoromethylated acrylic esters which are related to the compounds of the present invention. However, the method described is not desirable in the preparation of the 1,1,1-tri-fluoro-2-propene compounds of the present invention because of the possibility for halogen reduction prior to the formation of a trifluoromethylated hydroxyester intermediate and the effluent problems associated with the use of zinc.

The preparation of certain α-fluoro-α,β-unsaturated esters is the subject of Tetrahedron Letters 30, No. 41, pp 5571–5574 (1989). However, the α-fluoro-α,β-unsaturated esters are distinct from the compounds of the present invention and their preparation requires the use of pyrophoric reagents and low temperatures.

It is therefore an object of the present invention to provide 1,1,1-trifluoro-2-propene compounds useful in the preparation of insecticidal, acaricidal and nematicidal arylpyrrole compounds.

It is a further object of the invention to provide an efficient method of preparing the 1,1,1-trifluoro-2-propene compounds of the invention. These and other objects of the present invention will become evident by the detailed description set forth below.

SUMMARY OF THE INVENTION

The present invention describes 1,1,1-trifluoro-2-propene compounds that are useful intermediates in the preparation of certain etherocyclic compounds such as arylpyrroles.

The 1,1,1-trifluoro-2-propene compounds of the present invention are prepared via an efficient two step halogenation and elimination process using readily available starting materials and mild conditions.

The 1,1,1-trifluoro-2-propene compounds of the present invention have the structural formula I:

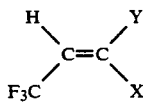

wherein
X is Cl, Br or I;
Y is CN, $CO_2R$ or $C(O)R_1$;
R and $R_1$ are hydrogen or $C_1$–$C_4$ alkyl; and the cis and trans isomers thereof.

Advantageously, it has been found that the 1,1,1-trifluoro-2-propene compounds of the present invention are useful in the preparation of insecticidal, acaricidal and nematicidal arylpyrrole compounds which are described in copending patent application Ser. No. 392,495, filed on Aug. 11, 1989 and which is incorporated herein by reference thereto.

DETAILED DESCRIPTION OF THE INVENTION

The compounds of the present invention are useful in the preparation of excellent insecticidal, acaricidal and nematicidal arylpyrrole compounds.

The 1,1,1-trifluoro-2-propene compounds of the present invention have the structural formula I:

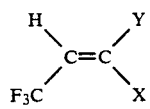

wherein
X is Cl, Br or I;
Y is CN, $CO_2R$ or $C(O)R_1$;
R and $R_1$ are hydrogen or $C_1$–$C_4$ alkyl; and the cis and trans isomers thereof.

Preferred 1,1,1-trifluoro-2-propene compounds of the invention are those in which X is Cl or Br; and R and $R_1$ are $C_1$–$C_4$ alkyl.

Formula I compounds may be prepared by reacting trifluoroacetaldehyde with (triphenylphosphoranylidene)acetonitrile in a solvent to give 4,4,4-trifluorocrotononitrile. The said 4,4,4-trifluorocrotononitrile or other compound having the structural formula II:

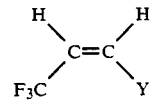

wherein
Y is CN, $CO_2R$ or $C(O)R_1$;
R and $R_1$ are $C_1$–$C_4$ alkyl; and the cis trans isomers thereof;
is reacted with at least about two molar equivalents, preferably about two to five molar equivalents of a halogenating agent int he presence of a solvent to form 2,3-dihalo-1,1,1-trifluoropropane compounds of formula III:

F₃CCHXCHXY         (III)

wherein
X is Cl, Br or I; and Y is as described above. Halogenating agents that may be employed include bromine, chlorine, iodine, and the like. Reaction solvents suitable for use in the above-described reaction include tetrahydrofuran, carbon tetrachloride and the like. The resultant 2,3-dihalo-1,1,1,-trifluoropropane is then reacted with at least about one molar equivalent, preferably about one to three molar equivalents, of a base in the presence of a solvent to form 1,1,1-trifluoro-2-propene compounds of formula I. Bases suitable for use in the reaction include triethylamine, pyridine and sodium carbonate and the like. Solvents such as ether and tetrahydrofuran may be preferably employed. This reaction scheme is illustrated as follows:

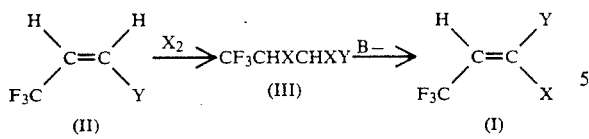

Certain starting formula II compounds are known in the art and may be prepared for example according to the methods described by H. Ogoshi, Journal of Organic Chemistry, 51, pp 2366-2368, (1986).

The preparation of formula I compounds was illustrated in the previous reaction scheme, except when R is hydrogen. To prepare the formula I compounds when R is hydrogen an additional hydrolysis step may be required. Hydrolysis of a formula I compound when R is not hydrogen yields another formula I compound having the same structure except that R is now hydrogen.

Certain arylpyrrole compounds useful as insecticides, acaracides and nematicides may be prepared as described in copending patent application Ser. No. 392,495, filed on Aug. 11, 1989 by reacting a formula I 1,1,1-trifluoro-2-propene compound with at least one equivalent of a 4-(substituted or unsubstituted phenyl)-2-(trifluoromethyl)-2-oxazolin-5-one represented by formula IV:

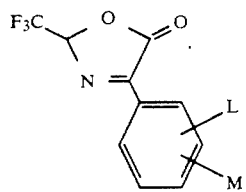

wherein

L is H, F, Cl or Br;

M is H, F, Cl, Br, I, $CF_3$, $NO_2$ or $OR_2$; and $R_2$ is $C_1$-$C_3$ alkyl or $C_2F_4H$;

and a base such as triethylamine, pyridine, sodium carbonate or the like in an organic solvent such as tetrahydrofuran, ether or the like to give a 2-(substituted or unsubstituted phenyl)-4,5-bis(trifluoromethyl)pyrrole having the structural formula V:

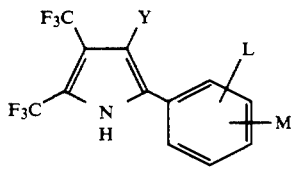

wherein

L, M, Y, R and $R_2$ are as described above. The reaction may be illustrated as follows:

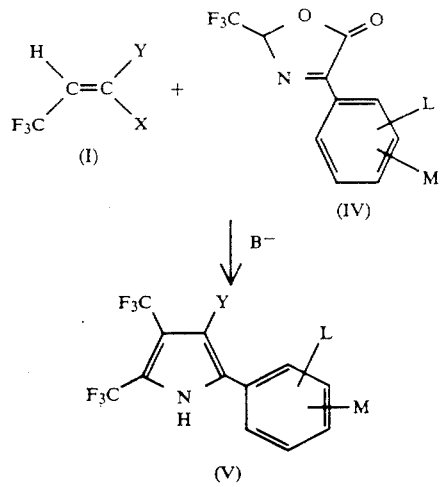

Arylpyrrole compounds of formula V may also be prepared by reacting a formula III 2,3-dihalo-1,1,1trifluoropropane compound and a base in a solvent with a solution of a formula IV 4-(substituted or unsubstituted phenyl)-2-(trifluoromethyl)-2-oxazolin-5-one and a base in a solvent to give a formula V arylpyrrole. Bases suitable for use in the reaction are triethylamine, pyridine, sodium carbonate and the like. Solvents used in the above reaction are tetrahydrofuran, ether and the like. The reaction may be illustrated as follows:

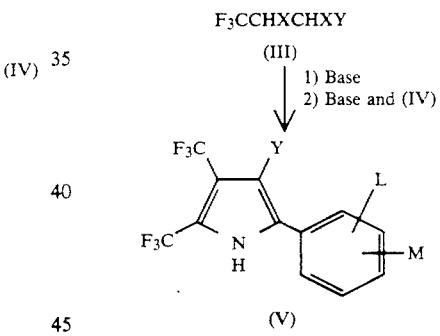

In order to facilitate a further understanding of the invention, the following examples are presented to illustrate more specific details thereof. The invention is not to be limited thereby except as defined in the claims.

EXAMPLE 1

Preparation of 4,4,4-Trifluorocrotononitrile (E)-and(Z)-

Trifluoroacetaldehyde (47.4 g, 0.48 mol), generated by addition of 1-ethoxy-2,2,2-trifluoroethanol (77.6 g, 0.48 mol) to polyphosphoric acid (300 mL) heated to 150°-180° C., is swept with nitrogen over 2 hours into a slurry of (triphenylphosphoranylidene) acetonitrile (97.3 g, 0.32 mol) in ether (400 mL). The reaction mixture is stirred overnight under nitrogen. After filtering off the solid triphenylphosphine oxide, the ether is distilled off to obtain an orange solution. Bulb to bulb distillation of the solution affords 2 fractions of the title compound as a clear colorless oil (14.3 g, 37%). Fraction 1 (bp 20°-40° C., 14 mm) contains a 6:1 mixture of (E):(Z). Fraction 2 (bp 40-50° C., 14 mm) contains a 2:1 mixture of (Z):(E). the fractions are identified by NMR analyses.

EXAMPLE 2

Preparation of 2,3-Dibromo-4,4,4-Trifluorobutyronitrile

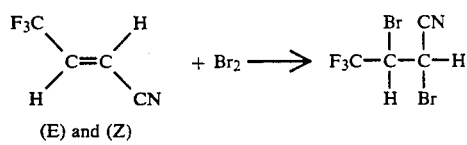

(E) and (Z)

Bromine (b 4,57 g, 0.029 mol) is added over a 5 minute period to a solution of 4,4,4-trifluorocrotononitrile (3,46 g, 0.029 mol) and carbon tetrachloride (70 mL). The resulting dark red solution is refluxed for 5 hours, then water (70 mL) is added to terminate the reaction. The organic layer is separated, washed sequentially with water, 5% sodium thiosulfate solution and water, dried over anhydrous magnesium sulfate, filtered and concentrated in vacuo to yield the title product as a yellow oil (6.1 g, 76%), identified by NMR spectral analyses.

Following the procedure of example 2, but substituting the appropriately substituted I,I,I-trifluoro-2-propene for 4,4,4-trifluorocrotononitrile yields the following compounds.

$$F_3C-\overset{Br}{\underset{H}{C}}-\overset{Y}{\underset{Br}{C}}-H$$

| Y | State |
|---|---|
| $\overset{O}{\underset{}{\|\|}}$<br>COCH₂CH₃ | colorless oil |
| $\overset{O}{\underset{}{\|\|}}$<br>CCH₃ | yellow oil |
| $\overset{O}{\underset{}{\|\|}}$<br>CH | yellow oil |

EXAMPLE 3

Preparation of 2Bromo-4,4,4-Trifluorocrotononitrile (E)- and (Z)-

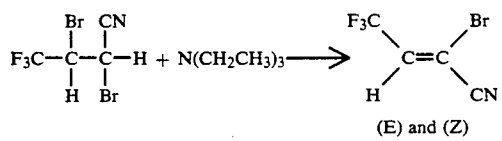

(E) and (Z)

Triethylamine (317 g, 0.037 mol) is added dropwise to a solution of 2,3-dibromo-4,4,4-trifluorobutyronitrile (5.32 g, 0.023 mol) and tetrahydrofuran (100 mL). A voluminous white precipitate forms during the addition. Stirring is continued for 1 hour, then the solid is filtered off and washed with tetrahydrofuran. The tetrahydrofuran is distilled off to give a dark brown oil. Bulb to bulb distillation (15 mm, 24° C.) of the oil yields the title product as a clear colorless liquid (3.1 g, 82%). NMR spectral analyses identifies a 6:1 mixture of E:Z.

Following the procedure described in example 3, but using the appropriately substituted 1,2-dibromo-3,3,3-trifluoropropane for 2,3-dibromo-4,4,4-trifluorobutyronitrile yields the compounds shown below.

$$\underset{H}{\overset{F_3C}{\diagdown}}C=C\underset{Y}{\overset{Br}{\diagup}}$$

(E) and (Z)

| Y | State |
|---|---|
| $\overset{O}{\underset{}{\|\|}}$<br>COCH₂CH₃ | clear yellow oil |
| $\overset{O}{\underset{}{\|\|}}$<br>CCH₃ | red oil |

EXAMPLE 4

Preparation of 2 (p-chlorophenyl)-4,5-bis(trifluoromethyl)pyrrole 3 carbonitrile

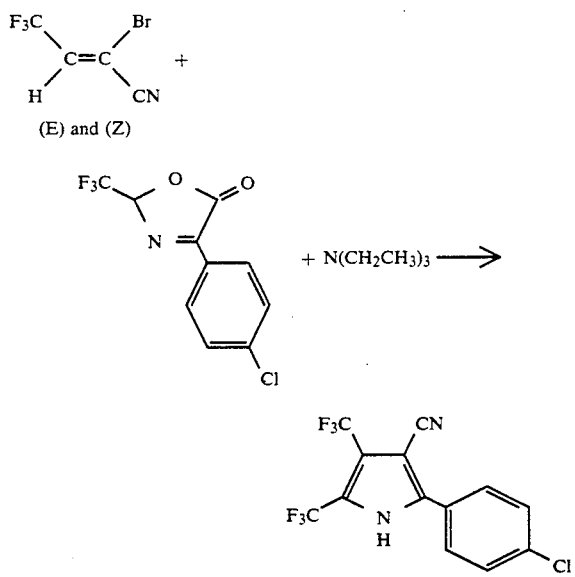

4-(p Chlorophenyl)-2-(trifluoromethyl)-2-oxazolin-5-one (2.0g, 7.59 mmol) and 2-bromo-4,4,4fluorocrotononitrile (0.81g, 4.05 mmol) are dissolved in acetonitrile (10 mL). To the resulting yellow solution triethylamine (0.45g, 4.46 mmol) is added dropwise while the reaction flask is cooled with a water bath. After stirring at 25° C. overnight, the reaction mixture is poured into water. The aqueous layer is extracted with ethyl acetate and the combined organic extracts are washed sequentially with water, 5% sodium thiosulfate solution and brine, dried over anhydrous magnesium sulfate and concentrated in vacuo to give a yellow solid. The solid is chromatographed using silica gel and eluted with hexane/ethyl acetate 3:1 to yield the title compound as yellow crystals (1.26 g, mp 208° C.).

Following the procedure of example 4, but substituting 3-bromo-5,5,5-trifluoro-3-penten-2-one for 2-bromo-4,4,4-trifluorocrotononitrile yields 2-(p- chlorophenyl) -4,5-bis (trifluoromethyl)pyrrole-3yl methylketone as yellow crystals.

EXAMPLE 5

Preparation of Ethyl 2-(p-chlorophenyl)-4,5-bis (trifluoromethyl)pyrrole-3-carboxylate

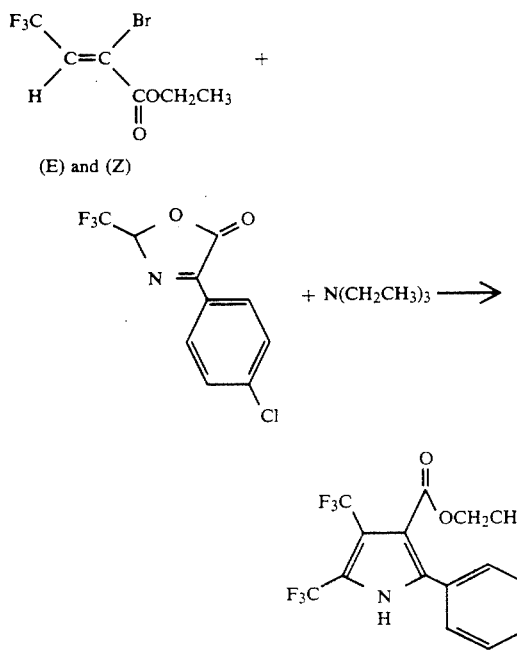

Triethylamine (1.1 g, 0.011 mol) is added dropwise to a solution of 4-(p-chlorophenyl)-2-(trifluoromethyl)-2-oxazolin-5-one (2.64 g, 0.01 mol) and acetonitrile (25 mL). After stirring for 10 minutes at room temperature, a solution of ethyl 2-bromo-4,4,4-trifluorocrotonate (2.47 g, 0.01 mol) and acetonitrile (1 mL) is added dropwise to the reaction mixture. The reaction mixture is stirred at room temperature for 2 hours then poured into water and extracted with ethyl acetate. The combined organic extracts are washed sequentially with water and brine, dried over anhydrous magnesium sulfate and concentrated in vacuo to give an orange oil which solidified upon standing. Trituration with hexanes gives the title product as a yellow solid (2.36 g, 61,3%, mp 138°-140° C.).

EXAMPLE 6

Preparation of 2-(3,4-dichlorophenyl)-4,5-bis(trifluoromethyl)pyrrole-3-carbonitrile

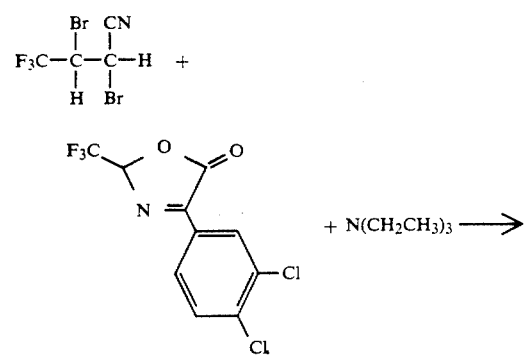

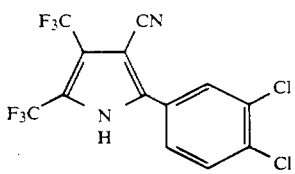

Triethylamine (0.59g, 5.83 mmol) is added dropwise to a solution of 2,3-dibromo-4,4,4-trifluorobutyronitrile (1.63g, 10.2 mmol) and tetrahydrofuran (20 mL). Stirring is continued for 15 minutes then a solution of 4-(3,4-dichlorophenyl)-2-(trifluoromethyl)-2- oxazlin-5-one (2.6 g, 8.72 mmol), triethylamine (0.88g, 8.7 mmol) and acetonitrile (5 ml) is added dropwise to the reaction mixture. The reaction mixture is stirred overnight at room temperature, poured into water and extracted with ethyl acetate. The combined organic extracts are washed sequentially with water and brine, dried over anhydrous magnesium sulfate and concentrated in vacuo to give a brown oil. Chromatography of the oil using silica gel and hexanes/ethyl acetate 3:1 yields the title product as a pale yellow solid (1.49g, 67%, mp 205°-208° C.)

What is claimed is:

1. A method for the preparation of a first compound having the structure:

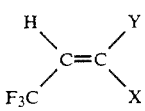

wherein
   X is Cl, Br or I;
   Y is CN, $CO_2R$ or $C(O)R_1$;
   R and $R_1$ are $C_1$–$C_4$ alkyl; and the cis and trans isomers thereof which comprises reacting a second compound having the structure

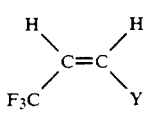

wherein Y is as described above; and the cis and trans isomers thereof with at least about 2 molar equivalents of a halogenating agent in the presence of a solvent to yield an intermediate compound having the structure

F$_3$CCHXCHXY wherein X and Y are as described above and reacting said intermediate with at least about one molar equivalent of a base in the presence of solvent to form said first compound.

2. The method according to claim 1, wherein the base is triethylamine, pyridine or sodium carbonate.

3. The method according to claim 1, wherein the halogenating agent is bromine or chlorine.

4. The method according to claim 1, wherein the reaction solvent is tetrahydrofuran, carbon tetrachloride or ether.

5. The method according to claim 1, wherein the temperature of the reaction mixture is about 10° to 100° C.

* * * * *

UNITED STATES PATENT AND TRADEMARK OFFICE
CERTIFICATE OF CORRECTION

PATENT NO. : 5,138,087

DATED : August 11, 1992

INVENTOR(S) : David G. Kuhn, Kenneth Alfred Martin Kremer

It is certified that error appears in the above-identified patent and that said Letters Patent is hereby corrected as shown below:

On the title page, Item [75] Inventors: "Kenneth A. Martin" should be --Kenneth A.M. Kremer--.

Signed and Sealed this

Nineteenth Day of October, 1993

*Attest:*

BRUCE LEHMAN

*Attesting Officer*   *Commissioner of Patents and Trademarks*